US012588842B2

(12) United States Patent
O'Donnell et al.

(10) Patent No.: US 12,588,842 B2
(45) Date of Patent: **\*Mar. 31, 2026**

(54) SYSTEMS AND METHODS FOR MEASURING OXYGEN IN A PATIENT'S BLOODSTREAM

(71) Applicant: Analog Devices International Unlimited Company, Limerick (IE)

(72) Inventors: John Jude O'Donnell, Quin (IE); Colin G. Lyden, Baltimore (IE); Michael C.W. Coln, Lexington, MA (US)

(73) Assignee: Analog Devices International Unlimited Company, Limerick (IE)

( \* ) Notice: Subject to any disclaimer, the term of this patent is extended or adjusted under 35 U.S.C. 154(b) by 0 days.

This patent is subject to a terminal disclaimer.

(21) Appl. No.: 18/654,910

(22) Filed: May 3, 2024

(65) Prior Publication Data

US 2024/0285197 A1     Aug. 29, 2024

Related U.S. Application Data

(63) Continuation of application No. 16/854,657, filed on Apr. 21, 2020, now Pat. No. 12,064,242, which is a
(Continued)

(51) Int. Cl.
*A61B 5/1455* (2006.01)
*A61B 5/00* (2006.01)
(Continued)

(52) U.S. Cl.
CPC ............ *A61B 5/14552* (2013.01); *A61B 5/00* (2013.01); *A61B 5/1455* (2013.01); *G01J 1/08* (2013.01);
(Continued)

(58) Field of Classification Search
CPC .............. A61B 5/1455; A61B 5/14552; A61B 5/14551; A61B 5/0261; G01J 1/08; G01J 1/00

See application file for complete search history.

(56) References Cited

U.S. PATENT DOCUMENTS 6,575,912 B1 \* 6/2003 Turcott ................... A61B 5/412
600/480
12,064,242 B2 \* 8/2024 O'Donnell ............ G01J 1/0228
(Continued)

FOREIGN PATENT DOCUMENTS

EP           3824810 B1     5/2024

OTHER PUBLICATIONS

"U.S. Appl. No. 16/854,657, Decision on Pre-Appeal Brief Request mailed Mar. 15, 2024", 2 pgs.
(Continued)

*Primary Examiner* — Jennifer Robertson
*Assistant Examiner* — Karen E Toth
(74) *Attorney, Agent, or Firm* — Schwegman Lundberg & Woessner, P.A.

(57) ABSTRACT

A photometry device can include a first LED to emit light to a target in response to a first current through the first LED, a second LED to emit light to the target in response to a second current through the second LED, and an inductor, coupled to the first and second LEDs, to store energy associated with at least one of the first and second currents.

18 Claims, 8 Drawing Sheets

Related U.S. Application Data continuation of application No. 15/622,846, filed on Jun. 14, 2017, now abandoned.

(51) Int. Cl.
    *G01J 1/08*         (2006.01)
    *G01J 1/46*         (2006.01)

(52) U.S. Cl.
    CPC ............... *G01J 1/46* (2013.01); *A61B 5/6826* (2013.01); *A61B 2560/0209* (2013.01)

(56) References Cited

U.S. PATENT DOCUMENTS

| | | | |
|---|---|---|---|
| 2016/0081602 A1* | 3/2016 | Lisogurki | A61B 5/029 600/476 |
| 2016/0143566 A1* | 5/2016 | Ballam | A61B 5/6826 600/323 |

OTHER PUBLICATIONS

"U.S. Appl. No. 16/854,657, Examiner Interview Summary mailed Jun. 14, 2023", 3 pgs.

"U.S. Appl. No. 16/854,657, Final Office Action mailed Oct. 2, 2023", 7 pgs.

"U.S. Appl. No. 16/854,657, Non Final Office Action mailed Feb. 27, 2023", 20 pgs.

"U.S. Appl. No. 16/854,657, Notice of Allowance mailed Apr. 17, 2024", 13 pgs.

"U.S. Appl. No. 16/854,657, Pre-Appeal Brief Request filed Feb. 1, 2024", 5 pgs.

"U.S. Appl. No. 16/854,657, Response filed Jun. 27, 2023 to Non Final Office Action mailed Feb. 27, 2023", 13 pgs.

"Korean Application Serial No. 10-2024-0054957, Notice of Preliminary Rejection mailed Dec. 18, 2024", w/ English machine translation, 6 pgs.

"Korean Application Serial No. 10-2024-0054957, Response filed Feb. 10, 2025 to Notice of Preliminary Rejection mailed Dec. 18, 2024", w/ English claims, 12 pgs.

* cited by examiner

SYSTEMS AND METHODS FOR MEASURING OXYGEN IN A PATIENT'S BLOODSTREAM

CLAIM OF PRIORITY

This application is a continuation of U.S. application Ser. No. 16/854,657, filed Apr. 21, 2020, which is a continuation of U.S. application Ser. No. 15/622,846, filed Jun. 14, 2017. The present application is based on and claims priority from the above applications, which are incorporated by reference herein in their entirety.

FIELD OF THE DISCLOSURE

The present disclosure relates to systems and methods for determining saturation of peripheral oxygen in a patient's bloodstream.

BACKGROUND

Certain photometry devices can sense a saturation of peripheral oxygen in a patient's bloodstream.

SUMMARY OF THE DISCLOSURE

In certain photometry systems, light can be provided by means of a power supply (e.g., a battery) a power regulating element (e.g., an LED driver) and a light source (e.g., an LED). The power regulating element may be comprised of more than one element (e.g. a voltage regulator and a linear current driver) or just one element (e.g., a linear current driver). In such systems, a large amount of power can be wasted in the electronics separating the power supply from the light emitting elements. For example, 100 mW of power can be consumed by the LED driver itself while 150 mW of power can be provided to the light emitting elements. The inventors have recognized, among other things, that it may be advantageous to use an inductor based driver and eliminate, at least, the use of the linear LED driver and possibly the voltage regulating element as well, such as to reduce an amount of power wasted in a photometry system, such as a photometry system that can sense a saturation of peripheral oxygen in a patient's bloodstream.

In an aspect, the disclosure can feature a photometry method. The method can include emitting light to at least a portion of a target using a variable amplitude current pulse, such as to generate the emitted light. The method can also include determining an amount of charge used in the variable amplitude current pulse. The method can also include detecting light received from the at least a portion of the target in response to the emitted light. The method can also include integrating a current associated with the received light in response to the emitted light. The method can also include determining a characteristic of the target using an indication of the integrated current and an indication of the amount of charge used in the variable amplitude current pulse. The method can also include emitting light at different wavelengths and measuring a differential response to determine a composition characteristic of the target. The method can also include collecting and storing the charge used in the variable amplitude current pulse. The method can also include recycling the stored charge used in the variable amplitude current pulse, such as to further emit light to the at least a portion of the target using an additional variable amplitude current pulse, and detecting light received from the at least a portion of the target in response to the further emitted light, and integrating a current associated with the received light in response to the further emitted light. The method can also include determining a characteristic of the target using an indication of the integrated current associated with the received light in response to the emitted light, an indication of charge used in the variable amplitude current pulse, an indication of the integrated current associated with the received light in response to the further emitted light, and an indication of charge used in the additional variable amplitude current pulse.

In an aspect, the disclosure can feature a photometry device. The photometry device can include a first LED, such as to emit light to a target in response to a first current through the first LED. The photometry device can also include a second LED, such as to emit light to the target, such as in response to a second current through the second LED. The photometry device can also include an inductor, such as can be coupled to the first and second LEDs, such as to store energy associated with at least one of the first and second currents. The photometry device can also include a switch, such as to selectively couple a terminal of the inductor to first and second reference voltage nodes. The photometry device can also include a capacitor, such as for forming a tank circuit with the inductor for storing energy. The charge can be stored on the capacitor using the first current through the first LED, and charge can be discharged from the capacitor using the second current through the second LED. The photometry device can also include a photosensitive element, such as to receive emitted light from the first LED and the second LED and integration circuitry, such as to determine a charge corresponding to an amount of light received from the first LED and the second LED. The photometry device can also include control circuitry, such as to determine a characteristic of the target using an indication of the charge corresponding to the amount of light received from the first LED and the second LED, and an indication of the charge stored on the first capacitor.

In an aspect, the disclosure can feature a system for photometry of a target. The system can include a first light emitting element, such as can be connected by a switching element to a first voltage source having a first voltage value, wherein the first light emitting element can transmit light through at least a portion of the target. The system can also include a charge storage element, such as to receive and store an amount of charge corresponding to a current delivered to the first light emitting element by the first voltage source. The system can also include control circuitry, such as to determine a first potential across the charge storage element, activate the switching element to connect the first voltage source to the first light emitting element, determine a second potential across the charge storage element, and determine an amount of charge stored on the charge storage element corresponding to an amount of light emitted by the first light emitting element from a difference between the second potential and the first potential. The system can also include a photosensitive element, such as to receive a portion of the light emitted by the first light emitting element and convert the received portion of light into an electrical signal, and integration circuitry, such as to integrate the electrical signal to determine an amount of charge corresponding to the amount of light received. The control circuitry can determine an amount of light absorbed by the portion of the target from a ratio of the amount of charge corresponding to an amount of light emitted by the first light emitting element and the amount of charge corresponding to the amount of light received. The system can also include a second light emitting element, such as can be connected by the switching element to a second voltage source having a second voltage value, wherein the second light emitting element can be configured to transmit light through the portion of the target, and the control circuitry can activate the switching element to deliver the charge stored on the charge storage element as a second electrical current through the second light emitting element. The photosensitive element can receive a portion of the light transmitted by the second light emitting element through the portion of the target. The control circuitry can determine a third electrical potential across the charge storage element, and determine an amount of charge corresponding to an amount of light emitted by the second light emitting element from a difference between the third electrical potential and the second electrical potential. The control circuitry can determine an amount of light absorbed by the portion of the target from a ratio of the amount of charge corresponding to an amount of light emitted by the second light emitting element and the amount of charge corresponding to the amount of light received from the second light emitting element. A wavelength of the first light emitting element can be different from a wavelength of the second light emitting element and a difference in light absorbed by the portion of the target between the first wavelength and the second wavelength can be used to provide a measure of peripheral $O_2$ saturation.

In an aspect, the disclosure can feature a photometry device. The photometry device can include an LED, such as to emit light to a target in response to a first current through the LED. The photometry device can also include an inductor, such as can be coupled to the LED, such as to store energy associated with the first current. The photometry device can also include a capacitor, such as can form a tank circuit with the inductor for storing energy. Charge can be stored on the capacitor using the first current through the LED, and charge can be discharged from the capacitor, such as to provide a second current through the LED. The photometry device can also include a plurality of switches, such as to reverse the polarity of the LED to allow the second current to flow from the capacitor and through the LED.

In an aspect, the disclosure can feature a photometry device. The photometry device can include a first LED, such as to emit light to a target in response to a current through the first LED. The photometry device can also include a first capacitor, such as to store charge from the current through the first LED. The photometry device can also include a second LED, such as to emit light to the target in response to current through the second LED provided by recycling stored charge from the first capacitor. The second LED can be antiparallel with the first LED. The photometry device can also include a first inductor, coupled to antiparallel arrangement of the first and second LEDs, such as to form an energy-storage tank circuit with the first capacitor. The photometry device can also include a switch, such as to selectively couple a first terminal of the first inductor to different first and second bias voltages.

BRIEF DESCRIPTION OF THE DRAWINGS

The present disclosure will now be described, by way of example, with reference to the accompanying drawings, in which.

DETAILED DESCRIPTION OF EMBODIMENTS OF THE DISCLOSURE

In a photometry device, a driver element (e.g., a linear current source) can provide power to one or more light emitting elements. The one or more light emitting elements can emit light to a target and a photosensitive element and detection circuitry can detect a portion of emitted light passing through the target. The detected fractions of emitted light passing through the target can provide an indication of a chemical concentration in the target, such as a saturated peripheral oxygen level. The inventors have recognized, among other things, that it may be advantageous to use an inductor based driver and eliminate the use of the linear element (e.g., a linear current driver, linear LED driver, or linear current source), such as to reduce an amount of power wasted in a photometry system. The use of an inductor based driver can disadvantageously provide variable amplitude current pulses to the one or more light emitting elements, whereas in photometry devices using a linear driver (e.g., a linear current driver, linear LED driver, or linear current source), the current pulses can be constant (e.g., the current pulses can be constant within 14 bits of accuracy during a time interval where an absorbance is being measured) such that system measurement accuracy is maintained. The inventors have additionally recognized, among other things, that the system inaccuracies, such as those introduced by the variation in the pulse amplitudes may be mitigated by storing and measuring an amount of charge corresponding to the variable amplitude current pulses provided to the one or more light emitting elements and to use an integrating transimpedance amplifier to determine an amount of light emitted by the one or more light emitting elements.

Figure 1A:
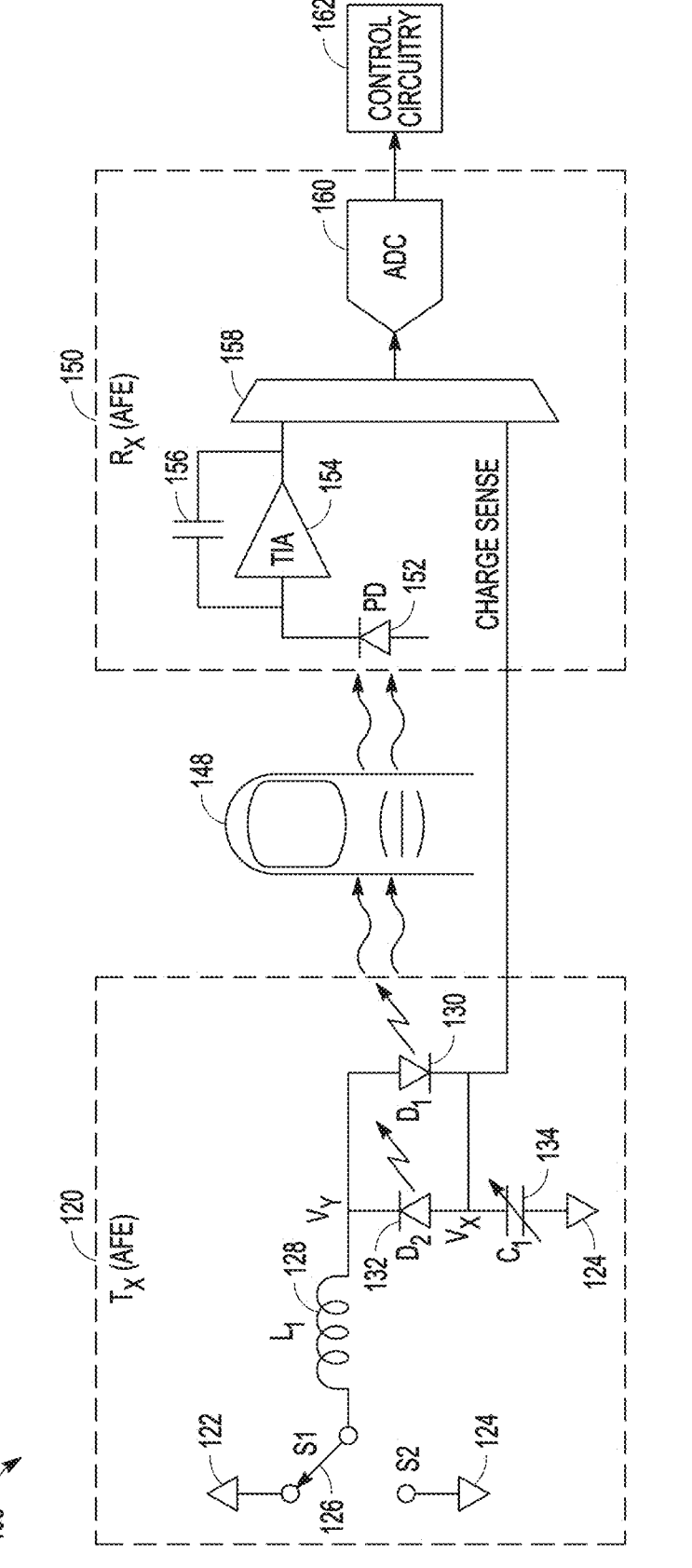
FIG. 1A illustrates a diagram of a photometry system.

FIG. 1A illustrates an example of a photometry system 100 operating with a reduced power consumption and having a self-quenching configuration. The photometry system 100 can include a transmitter 120 and a receiver 150. The transmitter 120 can include a first voltage source 122, an electrical ground 124, a switch 126, an inductor 128, a first light emitting diode 130, a second light emitting diode 132, and a programmable capacitor 134. The receiver 150 can include a photodiode 152, a transimpedance amplifier 154, a feedback capacitor 156, a multiplexer 158, an analog-to-digital converter 160, and control circuitry 162. The combination of the amplifier 154 and the feedback capacitor 156 constitutes an integrating transimpedance amplifier which those skilled in the art will recognize can be realised with various circuit configurations.

The switch 126 can be configured to connect either the first voltage source 122 or the electrical ground 124, to the inductor 128. The inductor can be connected to the switch 126, the first light emitting diode 130 and the second light emitting diode 132. The first light emitting diode 130 can be connected to the inductor 128 and the programmable capacitor 134. The second light emitting diode 132 can be connected to the inductor 128 and the programmable capacitor 134. The programmable capacitor 134 can be connected to the first light emitting diode 130, the second light emitting diode 132, an electrical ground 124, and the multiplexer 158. The photodiode 152 can be connected an input terminal of the transimpedance amplifier 154. The feedback capacitor 156 can be connected between an input terminal and an output terminal of the transimpedance amplifier 154. The output of the transimpedance amplifier 154 can be connected to the multiplexer 158. The output of the multiplexer 158 can be connected to the input of the analog-to-digital converter 160. The output of the analog-to-digital converter 160 can be connected to the control circuitry 162.

During operation, the switch 126 can be activated, such as to connect the first voltage source 122 to the inductor 128, such as to provide a first variable amplitude current pulse to the first light emitting diode 130. In an example, the first voltage source 122 can have a voltage value of about 5V. After activation of the switch 126, an increasing current can flow from the first voltage source 122 and through the inductor 128 and the first light emitting diode 130. In an example, a voltage drop across the first light emitting diode 130 can be about 1.5 V. A charge corresponding to the increasing current flowing through the first light emitting diode 130 can be stored by the programmable capacitor 134, such as can provide an increasing voltage at a node (Vx) of the transmitter 120. The increasing voltage at the node (Vx) can provide an increasing voltage at a node (Vy) of the transmitter 120, which in turn can provide a decreasing voltage drop across the inductor 128. The decreasing voltage drop across the inductor 128 can slow the rate of increase of current flow until a voltage drop across the inductor 128 is zero, at which time the current flowing through the first light emitting diode 130 can begin to decrease. The current flowing through the first light emitting diode 130 can then continue to decrease until the current through the first light emitting diode 130 is reduced to zero. The current decreasing to zero can be referred to as a self-quenching effect. A self-quenching effect can be desirable, such as to avoid the need for precisely timed switching elements. The shape of the first variable amplitude current pulse can include a half-sinusoidal shape 180, such as that shown in FIG. 1B. The shape of the first variable amplitude current pulse can be adjusted, such as by adjusting a capacitance value of the programmable capacitor 134 or by adjusting an inductance value of the inductor 128. A charge stored on the programmable capacitor 134 can correspond to the total charge provided to the first light emitting diode 130 by the first variable amplitude current pulse. The first light emitting diode 130 can emit light to a target 148 (e.g., a finger or earlobe), such as in response to the first variable amplitude current pulse provided to the first light emitting diode 130.

An amount of charge corresponding to the first variable amplitude current pulse provided to the first light emitting diode 130 can be determined by measuring a voltage drop across the programmable capacitor 134 before activating the switch 126 to connect the first voltage source 122 to the inductor 128 and again after the current through the first light emitting diode 130 has dropped to zero. The measured voltage drops can be provided to the multiplexer 158 and can be digitized by the analog-to-digital converter 160 before being provided to the control circuitry 162. The control circuitry 162 can determine a charge corresponding to the first variable amplitude current pulse from the measured voltage drops. The determined charge corresponding to the first variable amplitude current pulse can be used to normalize or compensate for variations in voltage supplied by the voltage source 122.

The photodiode 152 can receive light emitted by the target 140 in response to light emitted by the first light emitting diode 130. The transimpedance amplifier 154 and the feedback capacitor 156 can integrate a received signal from the photodiode 152 to provide an output signal to the multiplexer 158. The output signal provided by the transimpedance amplifier 154 can represent an amount of light received from the target 148 corresponding to the first variable amplitude current pulse. The multiplexer 158 can provide the output signal provided by the transimpedance amplifier 154 to the analog-to-digital converter 160. The analog-to-digital converter 160 can digitize the received output signal and can provide a digitized version of the output signal to the control circuitry 162.

The control circuitry 162 can then determine a first fraction of light emitted by the first light emitting diode 130 and received from the target 148 by the photodiode 152 by comparing the determined amount of charge corresponding to the first variable amplitude current pulse and an amount of light received from the target 148 corresponding to the first variable amplitude current pulse. The first fraction of light can be indicative of an absorbance of light emitted by the first light emitting diode 130 and absorbed by the target 148.

After the current corresponding to the first variable amplitude current pulse has decreased to zero and stopped flowing through the first light emitting diode 130, the switch 126 can be activated to connect the inductor 128 to the electrical ground 124, such as to recycle the charge stored on the programmable capacitor 134 and provide a second variable amplitude current pulse to the second light emitting diode 132. In an example, the activation of the switch 126 to connect the inductor 128 to the electrical ground 124 does not require precision timing because of the self-quenching configuration of the photometry circuit 100. After activation of the switch 126, an increasing current can flow from the programmable capacitor 134 and through the second light emitting diode 132 and the inductor 128. The current flowing from the programmable capacitor 134 can correspond to charge stored on the programmable capacitor 134 during activation of the first light emitting diode 130. The current flowing from the programmable capacitor 134 can reduce a stored charge on the programmable capacitor 134, such as can provide a decreasing voltage at the node (Vx). The decreasing voltage at the node (Vx) can provide a decreasing voltage at the first node (Vy), which in turn can provide a decreasing voltage drop across the inductor 128. The decreasing voltage drop across the inductor 128 can slow the rate of increase of current flow until a voltage drop across the inductor 128 is zero, at which time the current flowing through the second light emitting diode 132 can begin to decrease. The current flowing through the first light emitting diode 130 can then continue to decrease until the current through the second light emitting diode 132 is reduced to zero. In an example, the second light emitting diode 132 can be removed and further switching elements can be added, such as to provide the second variable amplitude current pulse to the first light emitting diode 130. The second light emitting diode 132 can emit light to the target 148 (e.g., a finger or earlobe), such as in response to the second variable amplitude current pulse provided to the second light emitting diode 132. In an example where the charge stored on the programmable capacitor 134 can be recycled to provide the second variable amplitude current pulse, a ratio of the charge corresponding to the first variable amplitude current pulse and the second variable amplitude current pulse can be independent of variations in a supply voltage, such as that provided by the voltage source 122.

An amount of charge corresponding to the second variable amplitude current pulse provided to the second light emitting diode 132 can be determined by measuring a voltage drop across the programmable capacitor 134 after activating the switch 126 to connect the electrical ground 124 to the inductor 128 and again after the current through the second light emitting diode 132 has dropped to zero. The measured voltage drops can be provided to the multiplexer 158 and can be digitized by the analog-to-digital converter 160 before being provided to the control circuitry 162. The control circuitry 162 can determine a charge corresponding to the second variable amplitude current pulse from the measured voltage drops. The determined charge corresponding to the second variable amplitude current pulse can be used to normalize or compensate for variations in voltage supplied by the voltage source 122.

The photodiode 152 can receive light emitted by the target 148 in response to light emitted by the second light emitting diode 132. The transimpedance amplifier 154 and the feedback capacitor 156 can integrate a received signal from the photodiode 152 to provide an output signal to the multiplexer 158. The output signal provided by the transimpedance amplifier 154 can represent an amount of light received from the target 148 corresponding to the second variable amplitude current pulse. The multiplexer 158 can provide the output signal provided by the transimpedance amplifier 154 to the analog-to-digital converter 160. The analog-to-digital converter 160 can digitize the received output signal and can provide a digitized version of the output signal to the control circuitry 162.

The control circuitry 162 can then determine a second fraction of light emitted by the second light emitting diode 132 and received from the target 148 by the photodiode 152 by comparing the determined amount of charge corresponding to the second variable amplitude current pulse and an amount of light received from the target 148 corresponding to the second variable amplitude current pulse. The second fraction of light can be indicative of an absorbance of light emitted by the second light emitting diode 132 and absorbed by the target 148.

In an example, a wavelength of the first light emitting diode 130 and the second light emitting diode 132 can be different and a peripheral oxygen saturation can be determined from the first fraction of light and the second fraction of light. In an example, a wavelength of the first light emitting diode 130 can be in the infrared band and a wavelength of the second light emitting diode 132 can be in the red band. In an example where a charge stored on the programmable capacitor 134 can be used to normalize or compensate a charge corresponding to an amount of light received by the photodiode 152, the impact of variations in a value of the voltage source 122 (e.g., the value of the voltage supply can have an average value of about 5V and can vary by about 20 mV) on the determined peripheral oxygen saturation can be reduced. For example, a peripheral oxygen saturation measurement can have an accuracy of about 0.1% where a charge stored on the programmable capacitor 134 can be used to normalize or compensate a charge corresponding to an amount of light received by the photodiode 152. In the absence of compensation or normalization using the charge stored on the programmable capacitor 134, the accuracy can be reduced very significantly (e.g., by as much as 40%) such as can be inadequate for medical purposes.

Figure 1B:
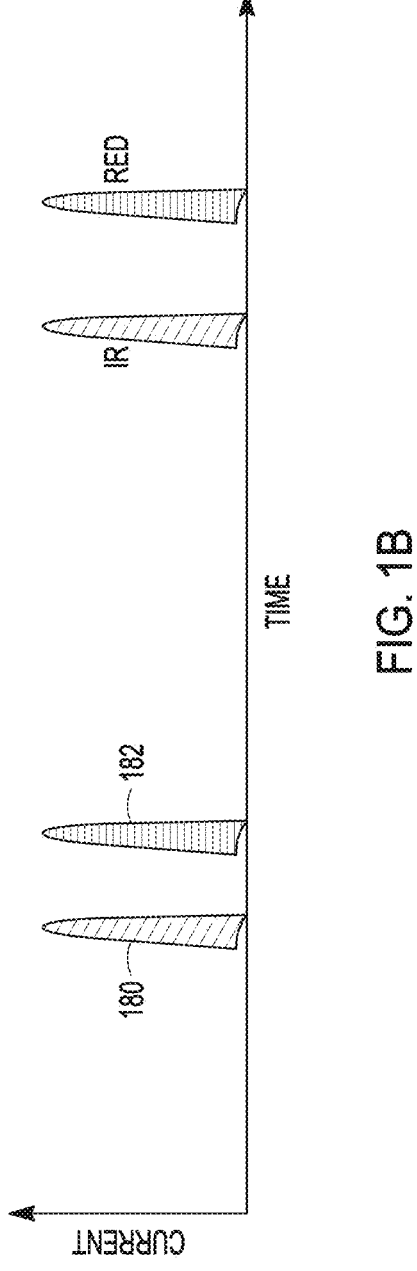
FIG. 1B illustrates a diagram of variable amplitude current pulses as a function of time.

FIG. 1B illustrates a diagram of variable amplitude current pulses as a function of time. The variable amplitude current pulses can be provided by a photometry system, such as the photometry system 100. A first variable amplitude current pulse 180 and a second variable amplitude current pulse 182 can be provided in succession. The first variable amplitude current pulse 180 and the second variable amplitude current pulse 182 can include a half-sinusoidal shape. In an example, the first variable amplitude current pulse 180 can be provided to a first light emitting diode, such as the first light emitting diode 130 that can then emit a first variable amplitude light pulse in response. The first variable amplitude light pulse can be an infrared light pulse. The second variable amplitude current pulse 182 can be provided to a second light emitting diode, such as the second light emitting diode 132 that can then emit a second variable amplitude light pulse in response. The second variable amplitude light pulse can be a red light pulse.

Figure 1C:
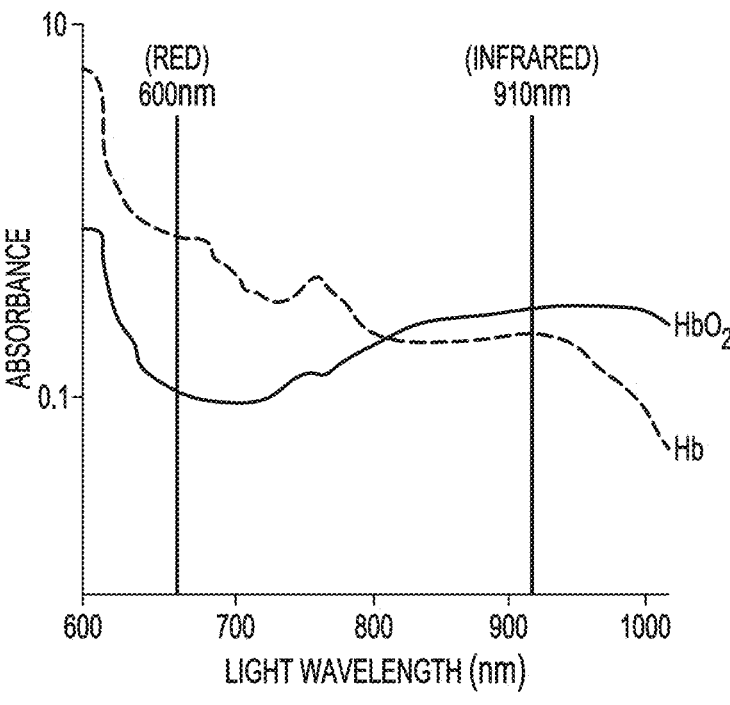
FIG. 1C illustrates an example of a diagram of absorbance of light as a function of a wavelength.

FIG. 1C illustrates an example of a diagram of absorbance of light as a function of a wavelength of light for hemoglobin (Hb) and oxygenated hemoglobin (HbO$_2$). The ratio of the absorbances of hemoglobin (Hb) and oxygenated hemoglobin can be significantly lower for infrared light than for red light. A saturated peripheral oxygen measurement can be determined from a difference in absorbance for red light and infrared light. In an example, the photometry system 100 can measure an absorbance of the target 148 for red light and for infrared light to determine a saturated peripheral oxygen of a patient.

Figure 1D:
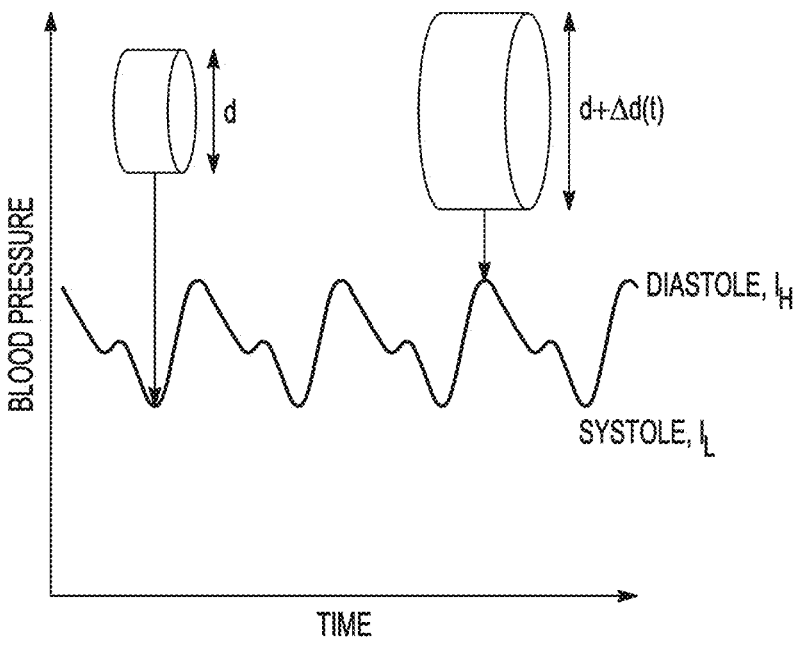
FIG. 1D illustrates a diagram of a patient's arterial volume as a function of time.

FIG. 1D illustrates a diagram of a patient's arterial volume as a function of time. The patient's arteries can be slightly elastic and can change volume in response to heartbeat pressure variations. In a saturated peripheral oxygen measurement, the control circuitry 162 can discriminate between light received from arteries and light received from finger, bone, tissue, or veins based at least in part on the changing arterial volume as a function of time.

Figure 1E:
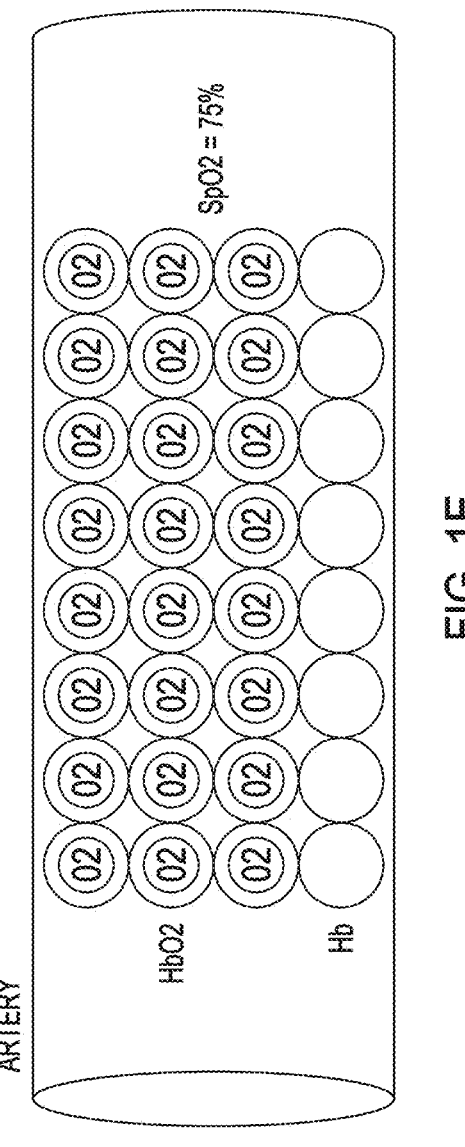
FIG. 1E illustrates a diagram of hemoglobin and oxygenated hemoglobin in a patient's artery.

FIG. 1E illustrates a diagram of hemoglobin and oxygenated hemoglobin in a patient's artery. A saturated peripheral oxygen measurement can correspond to a percentage of hemoglobin binding sites occupied by oxygen. In the example shown in FIG. 1E, 75% of the hemoglobin binding sites are occupied by oxygen, corresponding to a saturated peripheral oxygen of 75%. A healthy patient typically has over 95% of hemoglobin binding sites occupied by oxygen.

Figure 2A:
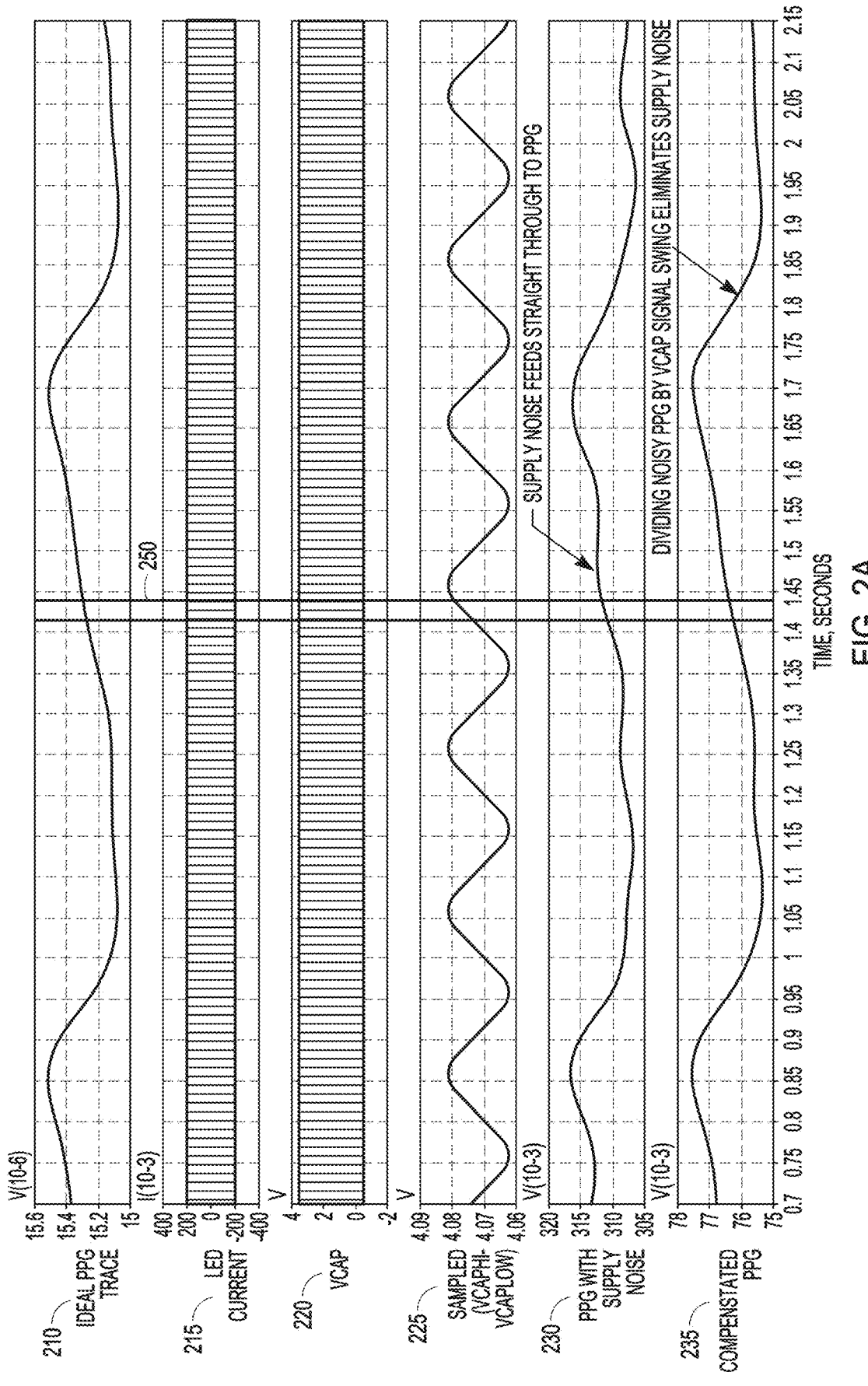
FIGS. 2A and 2B illustrate an example of operation of a photometry system.
Figure 2B:
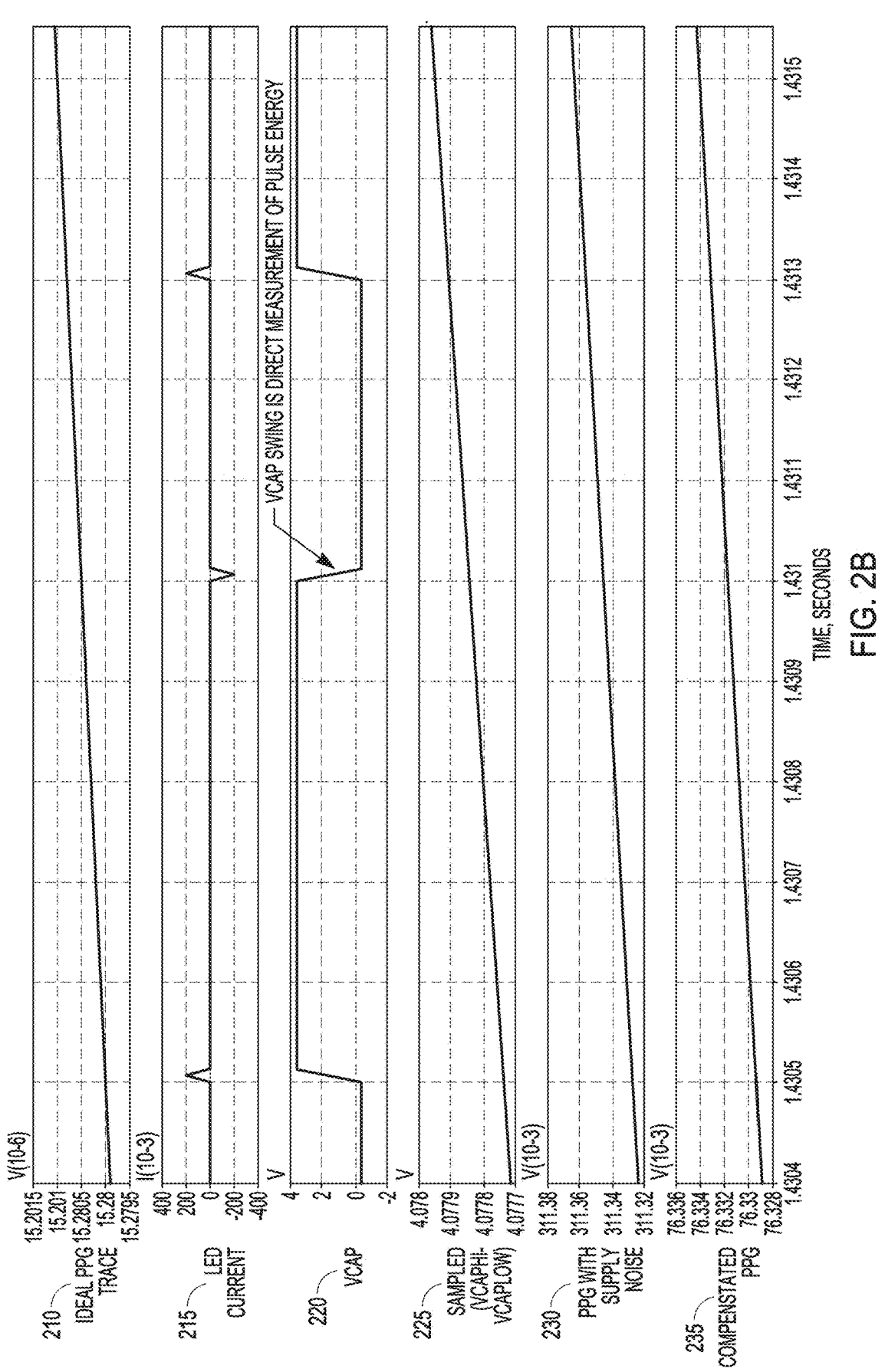

FIGS. 2A and 2B illustrate an example of simulated results in a photometry system, such as the photometry system 100 illustrated in FIG. 1, where the photometry system 100 can be used as a pulse oximeter to measure a peripheral oxygen saturation in a patient. FIG. 2B shows a zoomed-in region 250 of FIG. 2A. The simulated results can include an ideal photoplethysmogram trace 210, a light emitting diode current 215, a capacitor voltage 220, a difference between a sampled high voltage across a capacitor and a sampled low voltage across a capacitor 225, a photoplethysmogram trace including power supply noise 230, and a compensated photoplethysmogram 235. The ideal photoplethysmogram trace 210 can correspond to the situation where there is no noise introduced by a power supply, such as the first voltage source 122. The light emitting diode current 215 can correspond to current passing through the first light emitting diode 130 and the second light emitting diode 132. The capacitor voltage 220 can correspond to a voltage drop across the capacitor 134. The difference between the sampled high voltage across a capacitor and the sampled low voltage across a capacitor 225 can correspond to a measured voltage of the capacitor 134 before and after the first and second variable amplitude current pulses are delivered to the first and second light emitting diodes 130 and 132, respectively. The difference between the sampled high voltage across a capacitor and the sampled low voltage across a capacitor 225 can correspond to an amount of energy delivered by a variable amplitude current pulse, such as the first variable amplitude current pulse delivered to the first light emitting diode 130 and the second variable amplitude current pulse 132 delivered to the second light emitting diode 132. The photoplethysmogram trace 230 can correspond to the situation where there is noise introduced by a power supply, such as the first voltage source 122. The difference between the sampled high voltage across the capacitor and the sampled low voltage across the capacitor can be used to reduce or eliminate the supply noise present on the photoplethysmogram trace 230. In an example, the photoplethysmogram trace can be divided or normalized by the difference between the sampled high voltage across the capacitor and the sampled low voltage across the capacitor to reduce or eliminate noise introduced by the power supply.

Figure 3:
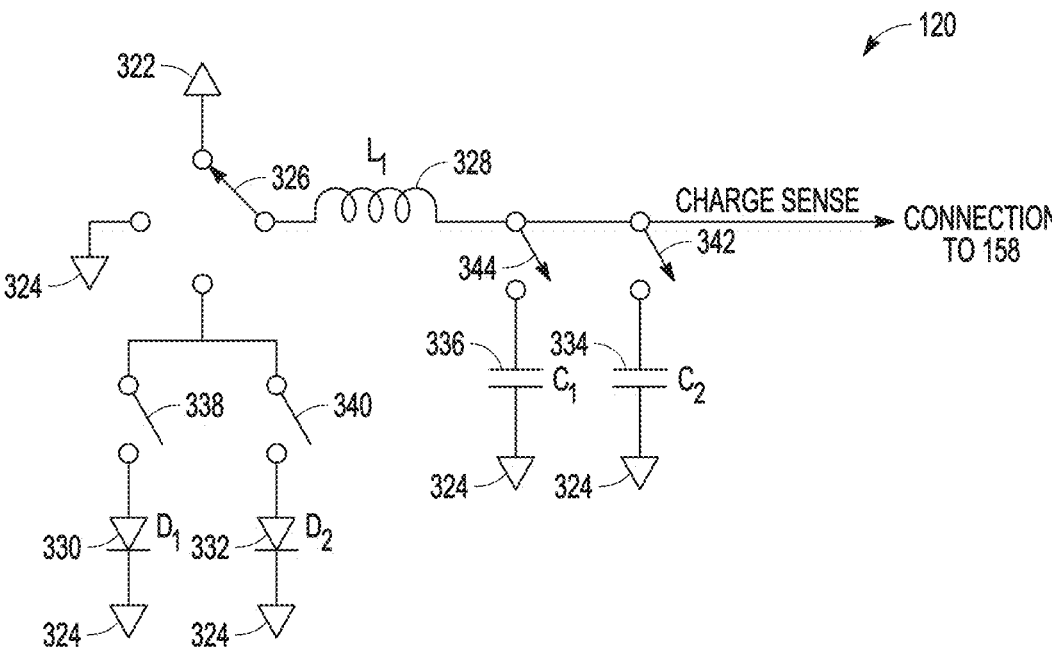
FIG. 3 illustrates an example of a transmitter in a photometry system.

FIG. 3 illustrates another example of a transmitter 120. The transmitter 120 can include an inductor 328, switches 326, 338, 340, 342, and 344, a first capacitor 336, a second capacitor 334, a first light emitting diode 330, a second light emitting diode 332, a voltage source 322, and an electrical ground 324. During operation, the switch 126 can be activated, such as to connect the voltage source 322 to the inductor 328. The switches 342 and 344 can also be activated, such as to connect the first capacitor 336, and the second capacitor 334 to the inductor 328. After activation of the switches 326, 342, and 344, a current can flow from the voltage source 322, through the inductor 328, and to the first capacitor 336, and the second capacitor 334. A charge corresponding to the current can be stored on the first and second capacitors 336 and 334. Similar to the transmitter 120 as described above, the current flowing to the first capacitor 336 and the second capacitor 334 can first increase, before deceasing to zero. After the current has stopped flowing to the first and second capacitors 336 and 334, the switches 326, 338, 340, 342, and 344 can be activated, such as to provide a connection from the first capacitor 336 to the first light emitting diode 330, while isolating the second capacitor 334, the voltage source 322, and the second light emitting diode 332. The charge stored on the first capacitor 336 can then flow through the first light emitting diode 330, such as to provide a first variable amplitude current pulse to the first light emitting diode 330. The first light emitting diode 330 can emit light to a target, such as the target 148, such as in response to the first variable amplitude current pulse provided to the first light emitting diode 330. After the current has stopped flowing to the first light emitting diode 330, the switches 326, 338, 340, 342, and 344 can be activated, such as to provide a connection from the second capacitor 334 to the second light emitting diode 332, while isolating the first capacitor 336, the voltage source 322, and the first light emitting diode 330. The charge stored on the second capacitor 334 can then flow through the second light emitting diode 332, such as to provide a second variable amplitude current pulse to the second light emitting diode 332. The second light emitting diode 332 can emit light to a target, such as the target 148, such as in response to the second variable amplitude current pulse provided to the second light emitting diode 332. In an example, after charging the first and second capacitors 336 and 334, the switch 326 can be activated, such as to connect the inductor 328 to an electrical ground 324, such as to moderate energy stored in the inductor 328 and the first and second capacitors 336 and 334. After moderating the energy, then each of the first and second capacitors 336 and 334 can be discharged to drive each the first and second light emitting diodes 330 and 332. In an example, the shape of the first variable amplitude current pulse and the second variable amplitude current pulse can be half-sinusoidal. The receiver 150 can receive and process the received light from the target 148, similar to that described above with respect to FIG. 1A.

Figure 4:
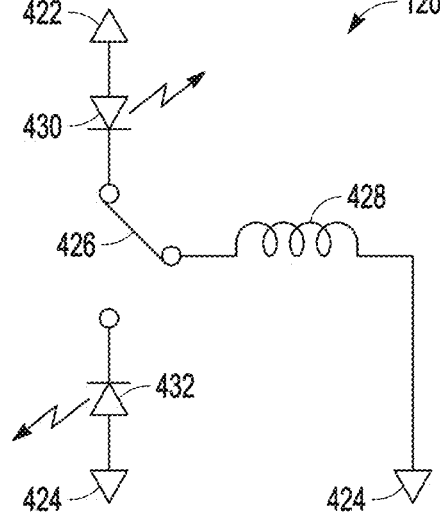
FIG. 4 illustrates an example of a transmitter in a photometry system.

FIG. 4 illustrates another example of a transmitter 120. The transmitter 120 can include a voltage source 422, an electrical ground 424, a switch 426, an inductor 428, a first light emitting diode 430, and a second light emitting diode 432. During operation, the switch can be activated, such as to connect the voltage source 422 to the inductor 428, such as to provide a first variable amplitude current pulse to the first light emitting diode 430. An increasing current can flow through the inductor 428 and the first light emitting diode 430. An amount of energy can be stored in a magnetic field of the inductor 428, such as due to the current flowing through the inductor. The first light emitting diode 430 can emit light to a target, such as the target 148, such as in response to the first variable amplitude current pulse provided to the first light emitting diode 430. The switch 426 can be activated, such as to disconnect the inductor from the voltage source 422 and connect the inductor to the second light emitting diode 432. The energy stored in the magnetic field of the inductor 428 can then be recycled and the inductor 428 can provide a second variable amplitude current pulse to the second light emitting diode 432. The second variable amplitude current pulse provided by the inductor 428 to the second light emitting diode 432 can correspond to the energy stored in a magnetic field of the inductor 428 during delivery of the first variable amplitude current pulse to the first light emitting diode 430. The second light emitting diode 432 can emit light to a target, such as the target 148, such as in response to the second variable amplitude current pulse provided to the second light emitting diode 432. In an example, the first variable amplitude current pulse and the second variable amplitude current pulse can be sawtooth shaped and the current through the inductor can be approximately triangular in shape. A magnitude of the variable amplitude current pulses can be adjusted by adjusting a value of the inductor 428. The receiver 150 can receive and process the received light from the target 148, similar to that described above with respect to FIG. 1A. In an example, the energy stored in the magnetic field of the inductor 428 can be determined by measuring the magnetic field, such as with a Hall device, a magnetoresistive sensor, or by adding another winding to the inductor 428 to make it a transformer and then monitoring a waveform on the second winding. The measured magnetic field can be used to normalize or compensate for variations in voltage supplied by the voltage source 422.

Figure 5:
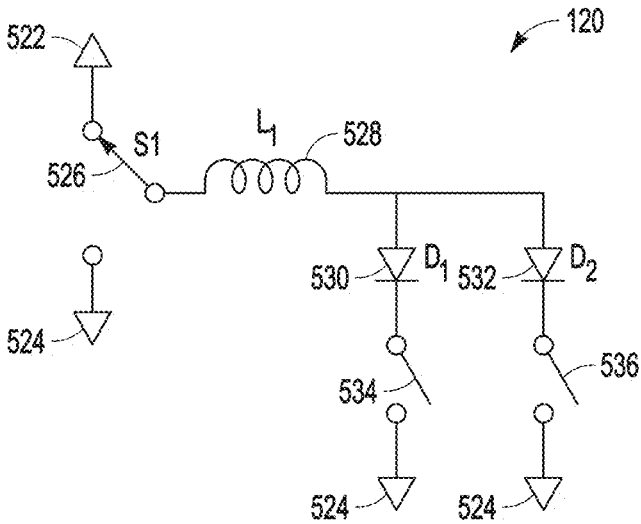
FIG. 5 illustrates an example of a transmitter in a photometry system.

FIG. 5 illustrates another example of a transmitter 120. The transmitter 120 can include a voltage source 522, an electrical ground 524, switches 526, 534, and 536, an inductor 528, a first light emitting diode 530, and a second light emitting diode 532. During operation, the switches 526, 534, and 536 can be activated, such as to connect the voltage source 522 to the inductor 528, such as to provide a first variable amplitude current pulse to the first light emitting diode 530. The switch 536 can prevent a current from flowing through the second light emitting diode 532. An increasing current can flow through the inductor 528 and the first light emitting diode 530. An amount of energy can be stored in a magnetic field of the inductor 528, such as due to the current flowing through the inductor 528. The first light emitting diode 530 can emit light to a target, such as the target 148, such as in response to the first variable amplitude current pulse provided to the first light emitting diode 530. The switch 526 can be activated, such as to disconnect the inductor 528 from the voltage source 522 and connect the inductor 528 to the electrical ground 524. The switches 534 and 536 can also be activated, such as to provide a second variable amplitude current pulse to the second light emitting diode 532. The switch 534 can prevent a current from flowing to the first light emitting diode 530. The energy stored in the magnetic field of the inductor 528 can then be recycled and the inductor 528 can provide a second variable amplitude current pulse to the second light emitting diode 532. The second variable amplitude current pulse provided by the inductor 528 to the second light emitting diode 532 can correspond to the energy stored in a magnetic field of the inductor 528 during delivery of the first variable amplitude current pulse to the first light emitting diode 530. The second light emitting diode 532 can emit light to a target, such as the target 148, such as in response to the second variable amplitude current pulse provided to the second light emitting diode 532. In an example, the first variable amplitude current pulse and the second variable amplitude current pulse can be sawtooth shaped and the current through the inductor can be approximately triangular in shape. A magnitude of the variable amplitude current pulses can be adjusted by adjusting a value of the inductor 528. The receiver 150 can receive and process the received light from the target 148, similar to that described above with respect to FIG. 1A. In an example, the energy stored in the magnetic field of the inductor 528 can be determined by measuring the magnetic field, such as with a Hall device, a magnetoresistive sensor, or by adding another winding to the inductor 528 to make it a transformer and then monitoring a waveform on the second winding. The measured magnetic field can be used to normalize or compensate for variations in voltage supplied by the voltage source 522.

Figure 6:
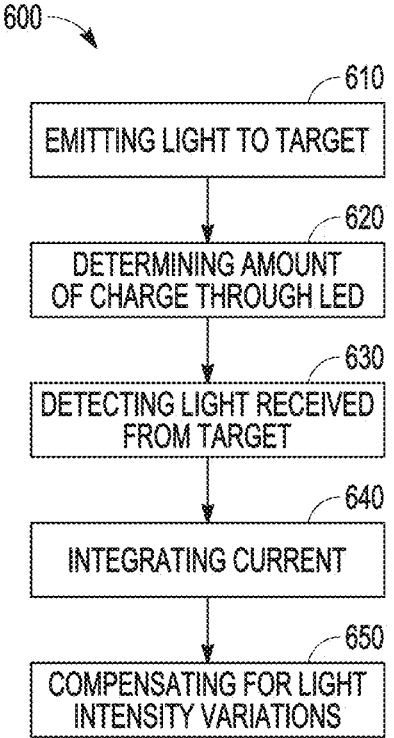
FIG. 6 illustrates a method of operation of a photometry system.

FIG. 6 illustrates a method of operation of a photometry system, such as the photometry system 100. A light emitting diode, such as the light emitting diode 130 or 132 can emit light to at least a portion of a target, such as the target 148 using a variable amplitude current pulse to generate the emitted light (step 610). Control circuitry, such as control circuitry 162 can determine an amount of charge used in the variable amplitude current pulse that passed through the light emitting diode, such as by measuring a voltage drop across a programmable capacitor, such as the programmable capacitor 134 (step 620). A photodiode, such as the photodiode 152 can detect light received from the at least a portion of the target in response to the emitted light (step 630). An integrating transimpedance amplifier, such as the transimpedance amplifier 154 and the feedback capacitor 156 can integrate a current associated with the received light in response to the emitted light (step 640). The control circuitry 162 can determine a characteristic of the target 148 using an indication of the integrated current and an indication of the amount of charge used in the variable amplitude current pulse, wherein the control circuitry 162 can compensate for light intensity variations of the light emitting diode by using the indication of the amount of charge used in the variable amplitude current pulse (step 650).

VARIOUS NOTES

Each of the non-limiting aspects described herein can stand on its own, or can be combined in various permutations or combinations with one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A photometry circuit for measuring a characteristic of a target, comprising:

a pulse sub-circuit configured to generate a first variable amplitude current pulse;

a first light source electrically coupled to the pulse sub-circuit, the first light source configured to receive the first variable amplitude current pulse from the pulse sub-circuit and emit first emitted light towards the target, the first emitted light being based on an amount of charge provided to the first light source by the first variable amplitude current pulse;

a first charge storage element electrically coupled to the first light source, the first charge storage element configured to store a stored amount of charge received from the first light source, the stored amount of charge being based on the amount of charge provided to the first light source by the first variable amplitude current pulse;

a photosensor positioned to detect first received light received from at least a portion of the target in response to the first emitted light;

an integrator configured to integrate a current associated with the first received light to generate a first integrated current indicating an amount of charge corresponding to the first received light;

a second light source;

a switch positioned to, when actuated, release the stored amount of charge stored at the first charge storage element to provide a second variable amplitude current pulse to the second light source, wherein the second light source is configured to emit second emitted light towards the target using the second variable amplitude current pulse; and a hardware control circuit configured to determine a characteristic of the target based at least in part on the first integrated current and the stored amount of charge.

2. The photometry circuit of claim 1, wherein the photosensor is positioned to detect second received light received from at least a portion of the target in response to the second emitted light, and wherein the integrator is configured to integrate a current associated with the second received light to generate a second integrated current.

3. The photometry circuit of claim 1, wherein the first light source emits the first emitted light at a first wavelength, and wherein the second light source emits the second emitted light at a second wavelength different than the first wavelength.

4. The photometry circuit of claim 3, wherein the hardware control circuit is further configured to use a difference in light absorbed by the portion of the target between the first wavelength and the second wavelength to provide a measure of peripheral $O_2$ saturation.

5. The photometry circuit of claim 1, wherein the switch is configured to selectively couple the first charge storage element to a first reference voltage or to a second reference voltage, wherein the first variable amplitude current pulse is generated when the switch couples the first charge storage element to the first reference voltage, and wherein the second variable amplitude current pulse is generated when the switch couples the first charge storage element to the second reference voltage.

6. The photometry circuit of claim 1, wherein the hardware control circuit is further configured to perform operations comprising:

before generating the first variable amplitude current pulse, determining a first potential across the first charge storage element;

after storing the stored amount of charge at the first charge storage element, determining a second potential across the first charge storage element; and determining the stored amount of charge using the first potential and the second potential.

7. The photometry circuit of claim 6, wherein the hardware control circuit is further configured to perform operations comprising determining an amount of light absorbed by the portion of the target using the stored amount of charge and the amount of charge corresponding to the first received light.

8. A photometry method for measuring a characteristic of a target, the method comprising:

generating a first variable amplitude current pulse;

emitting first emitted light towards the target using a first light source and the first variable amplitude current pulse;

storing a stored amount of charge at a first charge storage element electrically coupled to the first light source, the stored amount of charge being received from the first light source and based on an amount of charge provided to the first light source by the first variable amplitude current pulse;

detecting, using a photosensor, first received light received from at least a portion of the target in response to the first emitted light;

integrating a current associated with the first received light to generate a first integrated current indicating an amount of charge corresponding to the first received light;

actuating, using a hardware control circuit, a switch to release the stored amount of charge stored at the first charge storage element, wherein the releasing generates a second variable amplitude current pulse;

emitting second emitted light towards the target using the second variable amplitude current pulse and a second light source; and determining, using the hardware control circuit, a characteristic of the target based at least in part on the first integrated current and the stored amount of charge.

9. The photometry method of claim 8, further comprising:

detecting, using the photosensor, second received light received from at least a portion of the target in response to the second emitted light; and integrating a current associated with the second received to generate a second integrated current.

10. The photometry method of claim 9, wherein the determining of the characteristic of the target is also based at least in part on second received light and the second integrated current.

11. The photometry method of claim 8, wherein the first emitted light comprises light having a first wavelength and the second emitted light comprises light having a second wavelength different than the first wavelength, further comprising measuring a differential response to determine a composition characteristic of the target.

12. The photometry method of claim 11, wherein the characteristic of the target is a peripheral $O_2$ saturation.

13. The photometry method of claim 8, further comprising:

before generating the first variable amplitude current pulse, determining a first potential across the first charge storage element;

after storing the stored amount of charge at the first charge storage element, determining a second potential across the first charge storage element; and determining the stored amount of charge using the first potential and the second potential.

14. The photometry method of claim 13, further comprising determining an amount of light absorbed by the portion of the target using the stored amount of charge and the amount of charge corresponding to the first received light.

15. A photometry system for measuring a characteristic of a target, the photometry system comprising:

means for generating a first variable amplitude current pulse;

means for emitting first emitted light towards the target using the first variable amplitude current pulse;

means for storing a stored amount of charge, the stored amount of charge being received from the means for emitting first emitted light and based on an amount of charge provided to the means for emitting the first emitted light by the first variable amplitude current pulse;

means for detecting first received light received from at least a portion of the target in response to the first emitted light;

means for integrating a current associated with the first received light to generate a first integrated current indicating an amount of charge corresponding to the first received light;

means for releasing the stored amount of charge stored at the means for storing the amount of charge, wherein the releasing generates a second variable amplitude current pulse;

means for emitting second emitted light towards the target using the second variable amplitude current pulse; and means for determining a characteristic of the target based at least in part on the first integrated current and the stored amount of charge.

16. The photometry system of claim 15, further comprising:

means for detecting second received light received from at least a portion of the target in response to the second emitted light; and means for integrating a current associated with the second received light to generate a second integrated current.

17. The photometry system of claim 16, wherein the determining of the characteristic of the target is also based at least in part on second received light and the second integrated current.

18. The photometry system of claim 15, wherein the first emitted light comprises light having a first wavelength and the second emitted light comprises light having a second wavelength different than the first wavelength, further comprising means for measuring a differential response to determine a composition characteristic of the target.

* * * * *